United States Patent
Hsueh et al.

(10) Patent No.: US 9,707,393 B2
(45) Date of Patent: Jul. 18, 2017

(54) FEEDBACK-CONTROL WEARABLE UPPER-LIMB ELECTRICAL STIMULATION DEVICE

(75) Inventors: Ya-Hsin Hsueh, Yunlin (TW);
Chun-Yu Yeh, Yunlin (TW);
Hsin-Chang Lo, Yunlin (TW)

(73) Assignee: National Yunlin University of Science and Technology, Yunlin (TW)

( * ) Notice: Subject to any disclaimer, the term of this patent is extended or adjusted under 35 U.S.C. 154(b) by 177 days.

(21) Appl. No.: 14/240,793

(22) PCT Filed: Aug. 26, 2011

(86) PCT No.: PCT/CN2011/001429
§ 371 (c)(1),
(2), (4) Date: Mar. 23, 2015

(87) PCT Pub. No.: WO2013/029196
PCT Pub. Date: Mar. 7, 2013

(65) Prior Publication Data
US 2016/0144172 A1    May 26, 2016

(51) Int. Cl.
*A61N 1/00* (2006.01)
*A61N 1/36* (2006.01)
(Continued)

(52) U.S. Cl.
CPC ...... *A61N 1/36014* (2013.01); *A61B 5/04012* (2013.01); *A61B 5/0488* (2013.01);
(Continued)

(58) Field of Classification Search
CPC .............. A61N 1/36003; A61N 1/0452; A61N 1/36014; A61N 1/36103; A61N 1/36132;
(Continued)

(56) References Cited

U.S. PATENT DOCUMENTS 8,285,381 B2    10/2012 Fahey
2005/0165337 A1*    7/2005 Weiss ............... A61F 5/013
602/20

(Continued)

FOREIGN PATENT DOCUMENTS

CN    1088121 A    6/1994
CN    101243967 A    8/2008
CN    101244314 A    8/2008

*Primary Examiner* — Mallika D Fairchild
(74) *Attorney, Agent, or Firm* — Alan D. Kamrath; Kamrath IP Lawfirm, P.A.

(57) ABSTRACT

A feedback-control wearable upper-limb electrical stimulation device includes a plurality of electrical stimulation electrodes (10), a plurality of electromyography signal sensors (20), an electrical stimulation output unit (30), an electromyography signal acquisition unit (35), an electromyography signal operation unit (40), and a control module (50). Each electrical stimulation electrode (10) is adhered to or fixed in contact with a human trunk and applies an electrical stimulation signal to the neuromuscular system of the human trunk. Each electromyography signal sensor (20) is adhered to or fixed in contact with the human trunk at a corresponding position of the neuromuscular system of the human trunk where each electrical stimulation electrode (10) is disposed in an adhered manner. The electrical stimulation output unit (30) is connected to each electrical stimulation electrode (10) and provides an electrical stimulation signal. The electromyography signal acquisition unit (35) is connected to each electromyography signal sensor (20) and receives a myoelectric signal. The electromyography signal operation unit (40) is connected to the electromyography signal acquisition unit (35). The control module (50) is electrically connected to the electrical stimulation output unit (30) and the electromyography signal operation unit (40). The device first determines, according to the intensity of a myoelectric signal of a human trunk, the intensity of an (Continued)

electrical stimulation signal required for the human trunk to perform a specified action and gives a patient suitable assistance. Therefore, a local disabled limb of a patient can be effectively activated, and a patient can be effectively exercised in controlling a diseased limb.

18 Claims, 7 Drawing Sheets

(51) Int. Cl.
    *A61B 5/0488*    (2006.01)
    *A61N 1/04*    (2006.01)
    *A61B 5/00*    (2006.01)
    *A61B 5/04*    (2006.01)

(52) U.S. Cl.
    CPC .......... *A61B 5/4836* (2013.01); *A61B 5/6824* (2013.01); *A61N 1/0452* (2013.01); *A61N 1/36003* (2013.01); *A61B 5/04004* (2013.01); *A61B 5/6831* (2013.01); *A61B 5/7203* (2013.01); *A61B 5/725* (2013.01); *A61B 2505/09* (2013.01)

(58) Field of Classification Search
    CPC ............ A61N 1/36135; A61N 1/36139; A61B 5/0488; A61B 5/04888; A61B 5/04004; A61B 5/0024; A61B 2505/09
    See application file for complete search history.

(56) References Cited

U.S. PATENT DOCUMENTS

| | | | | |
|---|---|---|---|---|
| 2008/0234781 | A1* | 9/2008 | Einav | ................ A61N 1/36014 607/48 |
| 2010/0004715 | A1* | 1/2010 | Fahey | ................ A61H 39/002 607/48 |
| 2010/0130895 | A1* | 5/2010 | Armstrong | ........... A61H 1/0288 601/40 |
| 2011/0264002 | A1 | 10/2011 | Kolen et al. | |

* cited by examiner

FEEDBACK-CONTROL WEARABLE UPPER-LIMB ELECTRICAL STIMULATION DEVICE

BACKGROUND OF THE INVENTION

1. Field of Invention

This invention generally relates to an electrical stimulation device and, more particularly, to an electrical stimulation device that can be used on the upper limbs of human and provides a feedback control function.

2. Description of the Related Art

People may lose the ability to control their limbs entirely or partially, which is caused by a stroke, certain diseases or trauma. In order to prevent the atrophy of affected limbs and recover the ability of controlling the limbs that are paralyzed or partially disabled, physical treatment and rehabilitation should be given to the patient after being diagnosed.

For example, the stroke usually causes the hemiparesis or hemiplegia on the patient with different degrees and may be partial-ataxia or may result in losing control on local neuromuscular system, which results in muscle weakness. So far, how much rehabilitation is given to the patient depends on the different degree of paralysis, for example, by asking a patient to hold a rehabilitation cup and then to move it from a position to another repeatedly for training the paralysis or affected limb. For the patient who is in serious paralysis, a stretching exercise or an electrical stimulation can be given to the patient to stimulate the neuromuscular system of the patient's affected limbs and to assist the patient to do some rehabilitation movements such as stretching, retracting, opening the palm and clenching.

However, the conventional electrical stimulation is always given by the patient or a third person (for example, the rehab therapist) to stimulate the neuromuscular system of the affected limbs of the paralysis side via a controller, in order to achieve some assigning motions. Although the above-mentioned conventional electrical stimulation can make the affected limbs do the assigning motions and process the rehabilitation, the patient cannot control their limbs volitionally. The conventional electrical stimulation only can achieve a limited result and cannot train the patient to control the affected limbs of the paralyzed body side self-consciously.

Therefore, the conventional electrical stimulation of rehabilitation still has some inconvenience and defection, which needs to be further improved. In order to solve the above-mentioned problems, all the related manufacturers are eager to find the solutions. However, they still don't have any appropriate designs, and there are no products having appropriate designs that solve the above-mentioned problems.

SUMMARY OF THE INVENTION

The purpose of the invention is to overcome the limitation of a conventional electrical stimulation rehabilitation method or device that only can provide limb movement that is similar to physical treatment, but cannot provides training to the limb that is controlled by the patients self-consciously, and cannot integrate an electrical stimulation and an electromyography signal. As a result, the efficiency of the conventional electrical stimulation of rehabilitation is ineffective. The objective of the present invention is to provide a wearable upper limb electrical stimulation device with a feedback control function. This invention provides an integration of the electrical stimulation and an analysis of a volitional electromyography signal and a stimulus electromyography signal that cause a muscle contraction. This invention provides the appropriate assisting electrical stimulation for an affected limb according to the analyzed result of a volitional electromyography signal, which is able to obtain a fulfill rehabilitation achievement.

The present invention provides a wearable upper limb electrical stimulation device with a feedback control function comprising multiple electrical stimulation electrodes, multiple electromyography signal sensors, an electrical stimulation output unit, an electromyography signal acquisition unit, an electromyography signal operation unit and a control module. Each one of the electrical stimulation electrodes is pasted or attached to a human's limb, and the electrical stimulation is given to a neuromuscular system of the human's limb by each one of the electrical stimulation electrodes. In order to sense and receive the electromyography signal being generated by the human's limb, each one of the electromyography signal sensors is pasted or attached to the human's limb corresponding to a position of the neuromuscular system of human's limb where the electrical stimulation electrode is pasted. The electromyography signal thereof comprises the volitional electromyography signal, the stimulus electromyography signal and the interference signal. An electrical stimulation output unit is connected to each one of the electrical stimulation electrodes and provides the electrical stimulation. An electromyography signal acquisition unit is connected to each one of the electromyography signal sensors and successively receives, filters and amplifies the electromyography signal. The electromyography signal operation unit is connected to the electromyography signal acquisition unit and receives the electromyography signal which has been filtered and amplified. The control module is connected to the electrical stimulation output unit and the electromyography signal operation unit. The control module receives the electromyography signal via the electromyography signal operation unit and controls the electrical stimulation output unit according to the position and strength of the electromyography signal. The electrical stimulation output unit provides electricity to at least one electrical stimulation electrode for outputting the electrical stimulation to the human's body.

This invention's purpose and the technical problem which it solves can be realized by the technology below.

In the above-mentioned wearable upper limb electrical stimulation device with a feedback control function, the electromyography signal acquisition unit comprises an electrical stimulation signal blocking circuit, a instrumentation amplifier, an amplifier circuit, a high-pass and low-pass filter and a voltage level shifter or clamp circuit. The electrical stimulation signal blocking circuit filters the electromyography signal from interference by the electrical stimulation. The instrumentation amplifier performs a front-end amplification to the electromyography signal. The amplifier circuit increases an amplification ratio of the electromyography signal. The high-pass and low-pass filter filters the electromyography signal except for a setting range of the electromyography. The voltage level shifter or clamp circuit increases the voltage level of the electromyography signal. The above-mentioned wearable upper limb electrical stimulation device with a feedback control function further comprises an analog-to-digital converter connected between the voltage level shifter or clamper circuit and the electromyography signal operation unit. The analog-to-digital converter transfers the electromyography signal outputted from the voltage level shifter or clamper circuit, and the electromyography signal operation unit receives the digitized electromyography signal. The electromyography signal operation unit comprises an interference operation unit, a comb filter and a subtraction circuit. After the interference operation unit filters pulses of the electrical stimulation in the electromyography signal, the comb filter gets the volitional electromyography signal from the electromyography signal. The subtraction circuit generates the stimulus electromyography signal by subtracting the volitional electromyography signal from the electromyography signal.

The front-end signal of each electromyography signal is filtered by the interference operation unit with a predefined time range between 100 μs and 5 ms.

The above-mentioned wearable upper limb electrical stimulation device with a feedback control function further comprises a fixed brace being shaped corresponding to a human's limb. The fixed brace connects each one of the electrical stimulation electrodes, and each one of the electromyography signal sensors, the electrical stimulation output unit, the electromyography signal operation unit and the control module respectively, the electrical stimulation electrode and the electromyography signal sensor are mounted on an inner surface of the fixed brace.

In above-mentioned wearable upper limb electrical stimulation device with feedback control function, the fixed brace thereof comprises an upper arm fixed portion, a forearm fixed portion and a palm fixed portion being shaped respectively corresponding to an upper arm, a forearm and a palm of human, and is detachably mounted separately on the upper arm, the forearm and the palm.

The control module controls the corresponding electrical stimulation electrodes to generate the electrical stimulation according to the position and status of the received electromyography signal. The position of the electrical stimulation electrode corresponds to the neuromuscular system.

The control module may be a micro-processor module or a programmable chip.

The control module adjusts the electrical stimulation by using the electromyography signal. The control module defines the intensity of the electrical stimulation by using a comparison method or a look-up table method. The comparison method or the look-up table method compares the reading electromyography signal and a stored standard of electromyography signal and, then, outputs an appropriate electrical stimulation according to the result of the comparison. The stored standard of the electromyography signal is an electromyography signal value of a healthy limb or an average electromyography signal value of human.

The wearable upper limb electrical stimulation device with a feedback control function further comprises multiple flex/band sensors connected to the fixed brace corresponding to joints of the upper arm, the forearm and the palm of the human respectively. The flex/band sensors sense the curvature of the joints, and transfers the curvature to the control module. The control module controls the electrical stimulation output unit through a specific electrical stimulation electrode according to the curvature of the flex/band sensors and the electromyography signal.

The present invention has advantages and benefits as follows.

First, the present invention provides a suitable intensity of the electrical stimulation for a patient's limb to execute a specific movement or action, and provides an appropriate assist to the patient according to the received strength of the electromyography signal of the limb. Thus, the present invention not only activates the patient's partially disabled limb, but also can train the patient to have the ability to control the affected limb effectively.

In summary, the present invention relates to a wearable upper limb electrical stimulation device with a feedback control function having multiple electrical stimulation electrodes, multiple electromyography signal sensors, an electrical stimulation output unit, an electromyography signal operation unit and a control module. The present invention identifies the intensity of the electrical stimulation to provide an appropriate assist to the patient's limb to execute a specific movement according to the strength of the electromyography signal of the limb.

Even though numerous characteristics and advantages of the present invention have been set forth in the foregoing description, together with details of the structure and features of the invention, the disclosure is illustrative only. Changes may be made in the details, especially in matters of shape, size and arrangement of parts within the principles of the invention to the full extent indicated by the broad general meaning of the terms in which the appended claims are expressed.

DETAILED DESCRIPTION OF THE INVENTION

Figure 1:
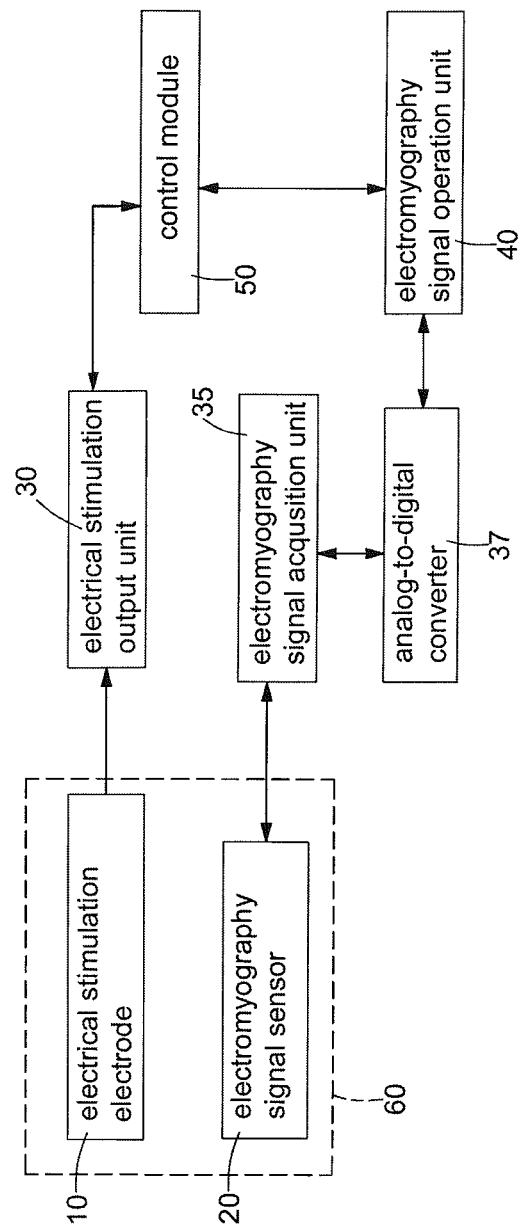
FIG. 1 is a block diagram of a preferred embodiment in accordance with the present invention.
Figure 2:
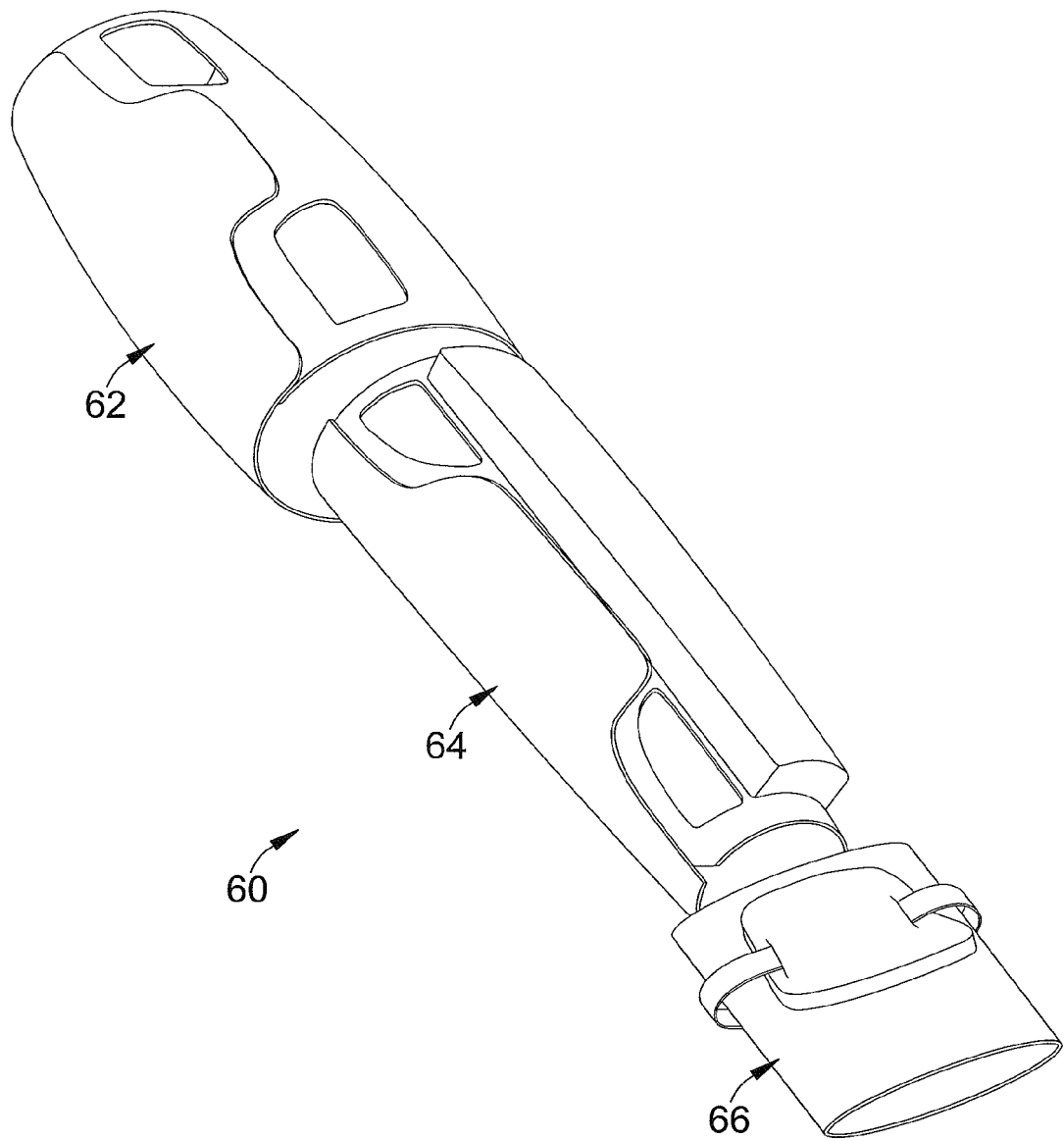
FIG. 2 is a perspective view of a fixed brace of the present invention.

With reference to FIGS. 1 and 2, a preferred embodiment of a wearable upper limb electrical stimulation device with feedback control function in accordance with the present invention comprises multiple electrical stimulation electrodes 10, multiple electromyography signal sensors 20, an electrical stimulation output unit 30, an electromyography signal acquisition unit 35, an analog-to-digital converter 37, an electromyography signal operation unit 40, a control module 50 and a fixed brace 60.

Figure 3:
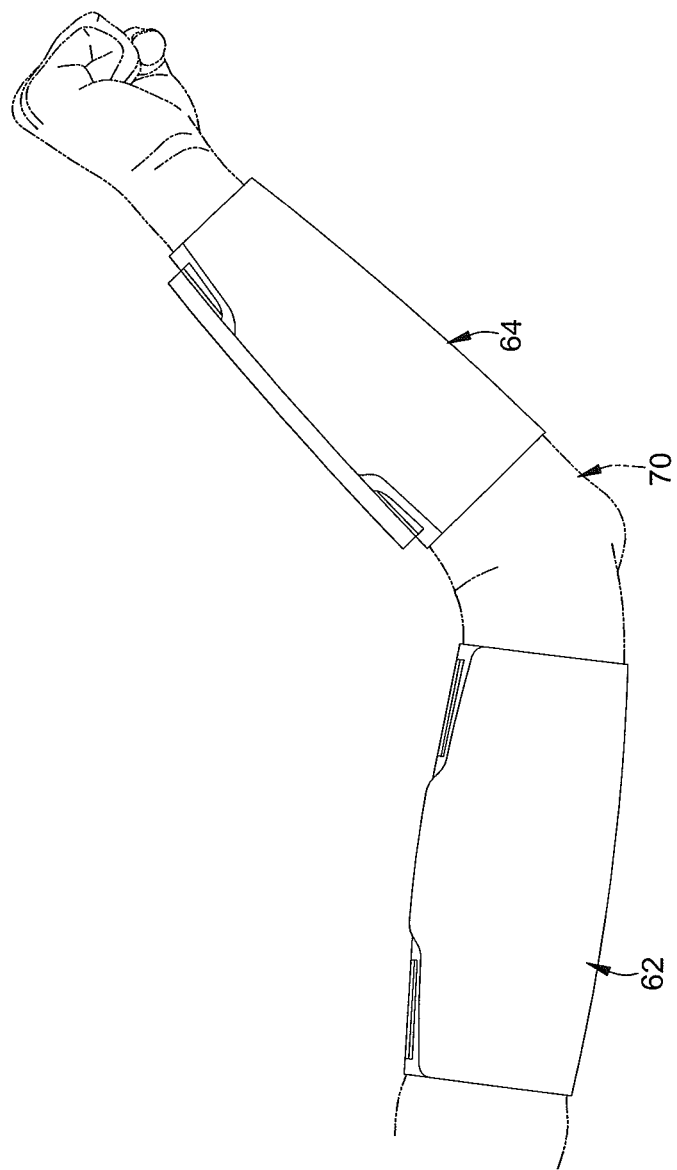
FIG. 3 is an operational perspective view of the preferred embodiment of the present invention.
Figure 4:
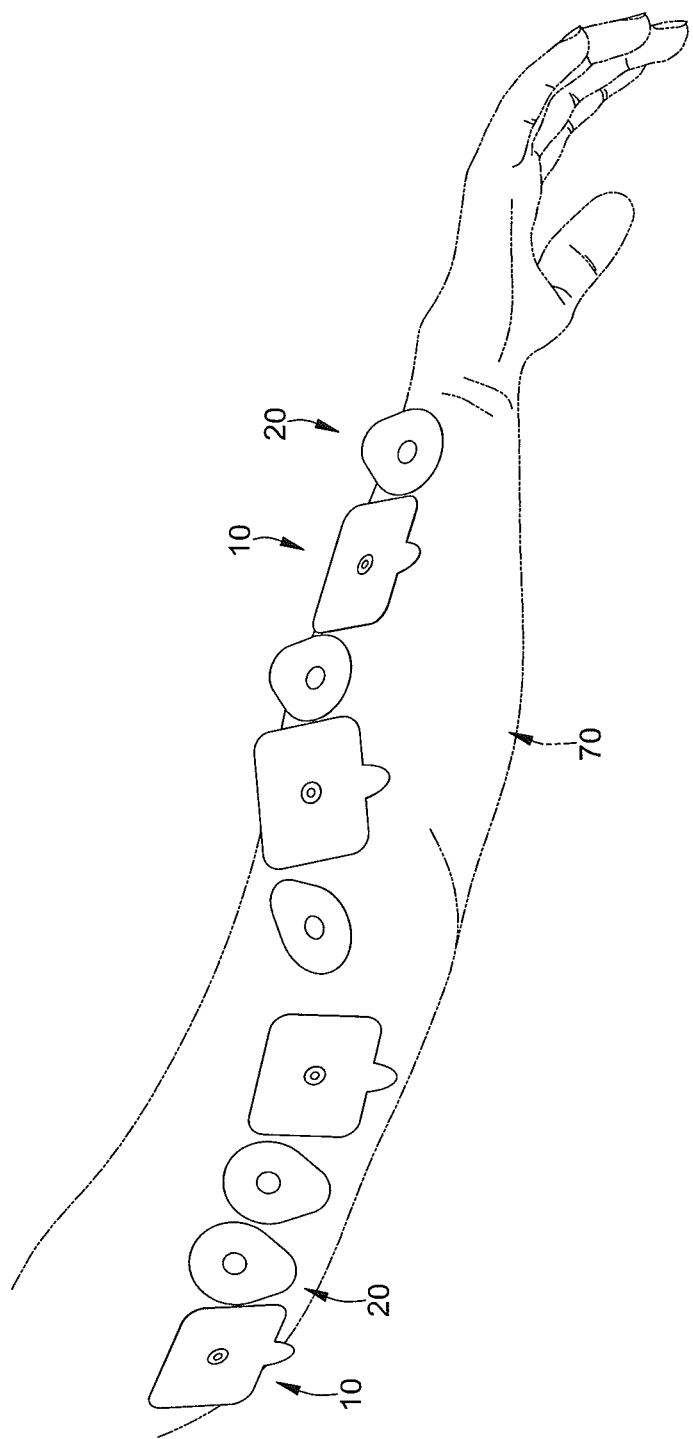
FIG. 4 is an operational perspective view of the pasted position of electrical stimulation electrodes and an electromyography signal sensors of the preferred embodiment of the present invention.
Figure 5:
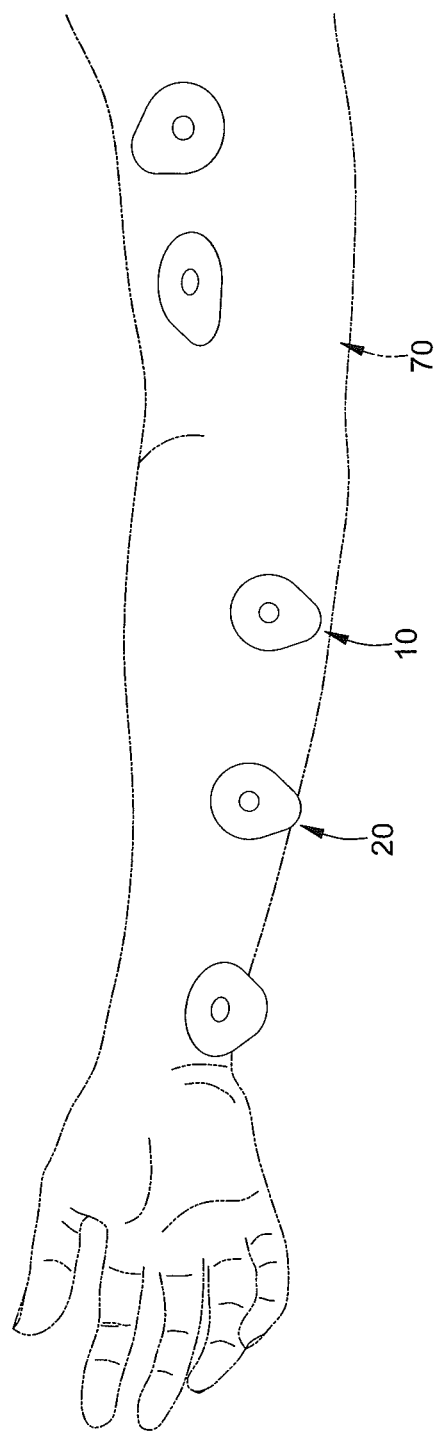
FIG. 5 is another operational perspective view of the pasted position of the electromyography signal sensors of the preferred embodiment of the present invention.

With reference to FIGS. 3 to 5, FIG. 3 is an operational perspective view of the preferred embodiment of the present invention. FIG. 4 is an operational perspective view of the pasted position of the electrical stimulation electrode 10 and the electromyography signal sensor 20 of the preferred embodiment of the present invention. FIG. 5 is another operational perspective view of the pasted position of the electromyography signal sensor 20 in the preferred embodiment. Each one of the electrical stimulation electrodes 10 is detachably attached or pasted to a human's limb 70. The human's limb 70 is an arm. Each one of the electrical stimulation electrodes 10 is controlled to provide an electrical stimulation to a neuromuscular system of the arm in an appropriate time. For example, each one of the electrical stimulation electrodes 10 is attached to an extensor muscle, a flexor muscle, a triceps brachii, or an extensor digitorum muscle, and provides an appropriate intensity of the electrical stimulation to stimulate the muscles of the neuromuscular system to perform corresponding movements.

The appropriate time is a time to output the electrical stimulation to a different muscle group to make an arm move forward, to a palm open or grip and to do similar actions. The appropriate intensity provides a suitable intensity of the electrical stimulation to assist relevant muscles based on characteristics of the neuromuscular system or the muscle groups. The appropriate intensity may be decided by pretesting or recording the intensity of the electrical stimulation that each muscle group of a hemiparesis or hemiplegia limb requires to generate a same or similar movement of a normal limb. Thus, the present embodiment may have an intensity of the electrical stimulation for the different muscle group to execute different movements. Therefore, each electrical stimulation electrode 10 may be controlled to output an electrical stimulation with suitable intensity for a specific movement that the relevant muscle group requires.

Each one of the electromyography signal sensors 20 is attached or pasted to the human's limb 70 and is correspondingly located on each muscle group of the neuromuscular system of the human's limb 70. The electromyography signal sensor 20 detects and continuously receives an electromyography signal from the human's limb 70, and the electromyography signal comprises a volitional electromyography signal, a stimulus signal and an interference signal.

The electromyography signal is a potential signal generated by the muscle relative to a movement of the muscle. The electromyography signal is proportional to an activation state of the muscle of the human's limb 70. Therefore, the activation states of the neuromuscular system of the human's limb 70 may be quantized by analyzing the electromyography signal. Since the electromyography signal is relative to information about the activation state of the muscle, and when the human's limb 70 of the embodiment receives the electrical stimulation from the electrical stimulation electrodes 10, the muscle of the human's limb 70 responds a voluntary contraction accordingly, which is a source of the volitional electromyography signal. Furthermore, the electromyography signal is directly evoked by giving the electrical stimulation to the muscle and is known as a stimulus electromyography signal. The electrical stimulation causes interference to the electromyography signal.

The electrical stimulation output unit 30 is connected to each one of the electrical stimulation electrodes 10. The electrical stimulation output unit 30 generates the electrical stimulation to each one of the electrical stimulation electrodes 10 for the human's limb 70.

Figure 6A:
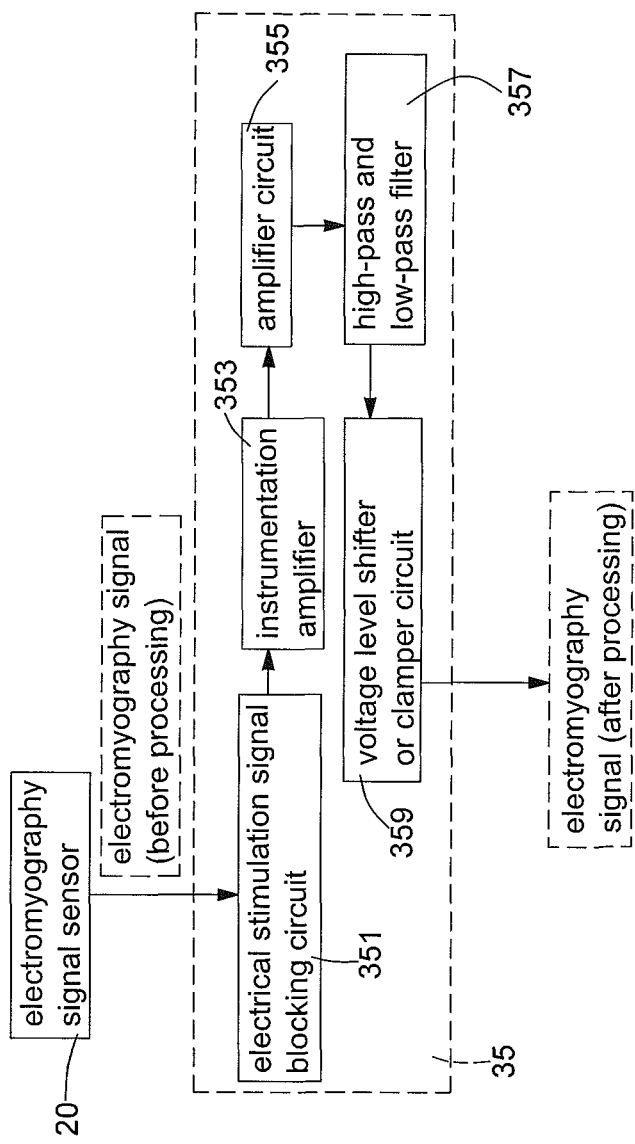
FIG. 6A is a circuit block diagram of an electromyography signal acquisition unit of the preferred embodiment of the present invention.
Figure 6B:
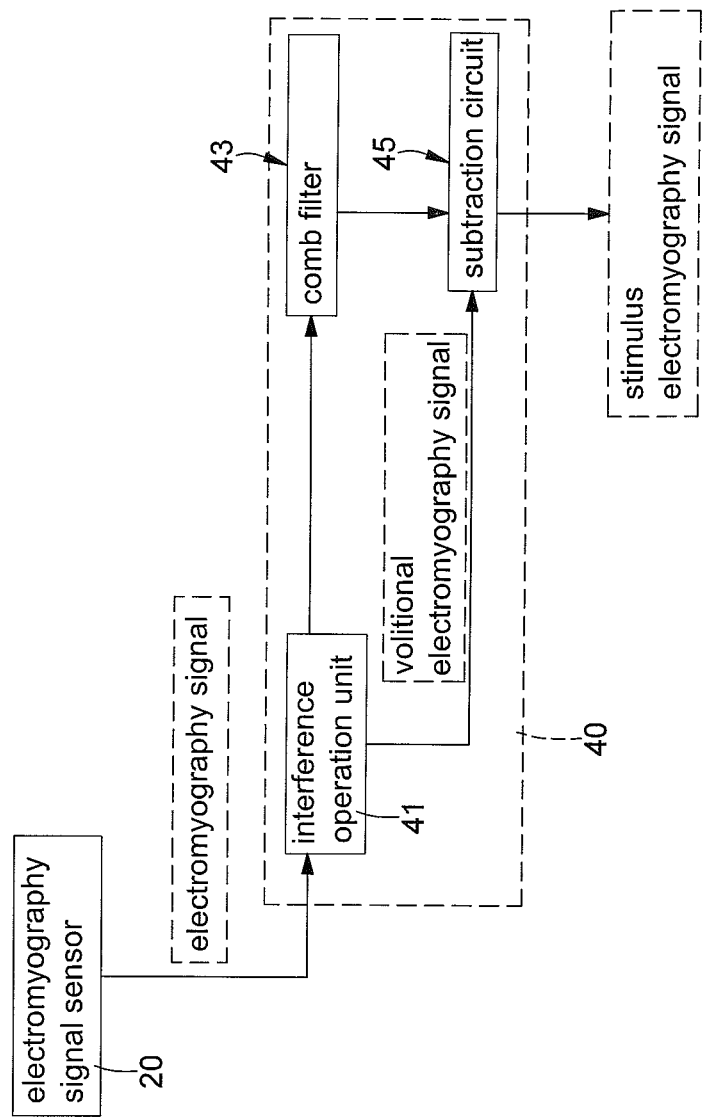
FIG. 6B is a circuit block diagram of an electromyography signal operation unit of the preferred embodiment of the present invention.

With reference to FIGS. 6A and 6B, the electromyography signal acquisition unit 35 is connected with each one of the electromyography signal sensors 20, which receives electromyography signals from the electromyography signal sensors 20. The electromyography signal acquisition unit 35 has an electrical stimulation signal blocking circuit 351, an instrumentation amplifier 353, a high-pass and low-pass filter 357 and a voltage level shifter or clamper circuit 359. In the preferred embodiment, the electrical stimulation signal blocking circuit 351 eliminates the electrical stimulation from the raw electromyography signal. The electrical stimulation signal blocking circuit 351 may have an OP amplifier circuit that is used to preliminarily eliminate the electrical stimulation from the electromyography signal to reduce interference.

As the raw electromyography signal is very weak, it needs to be amplified before being processed. First, the electromyography signal is processed by a front-end amplification through the instrumentation amplifier 353. Secondly, an amplification ratio of the electromyography signal is enhanced by amplifier circuit 355. Thirdly, the electromyography signal is then filtered by the high-pass and low-pass filter 357. The high-pass and low-pass filter 357 filters frequencies outside a defined range of 1 Hz to 1000 Hz and also filters a noise frequency. Finally, the electromyography signal is inputted to the voltage level shifter or the clamp circuit 359 to boost voltage levels of the electromyography signal.

The analog-to-digital converter 37 is connected to the electromyography signal acquisition unit 35. After receiving the electromyography signal outputted from the voltage level shifter or clamp circuit 359, the analog-to-digital converter 37 transfers the electromyography signal to a digital signal.

The electromyography signal operation unit 40 is connected to the electromyography signal acquisition unit 35, which receives the electromyography signal and outputs the electromyography signal after a signal processing (for example, filtering or clamping). In order to separate the volitional electromyography signal of the electromyography signal, the stimulus electromyography signal and the interference signal, with reference to FIG. 6B, the electromyography signal operation unit 40 comprises a serial interference operation unit 41, a comb filter 43 and a subtraction circuit 45. The interference operation unit 41 may filter a partial or predefined section of each electromyography signal. The interference operation unit 41 may eliminate or give a fixed value or a mean value, or it can use an algorithm to process the front section of each electromyography signal.

The interference signal of the electromyography signal is mainly caused by the electrical stimulation that is provided to the human's limb 70, and the electrical stimulation is normally a big pulse signal compared to the electromyography signal. Therefore, the interference operation unit 41 eliminates a section having the electrical stimulation in a time domain of the electromyography signal, for example, 100 μs to 5 ms in the time domain of each electromyography signal.

The comb filter 43 then separates the volitional electromyography signal from the electromyography signal and transmits the volitional electromyography signal to the subtraction circuit 45. The subtraction circuit 45 uses the electromyography signal which is processed by the interference operation unit 41 to substrate the volitional electromyography signal generated from the comb filter 43 and to receive the stimulus electromyography signal afterward.

The control module 50 is connected to the electrical stimulation output unit 30 and the electromyography signal operation unit 40. The control module 50 controls the electrical stimulation output unit 30 to provide electrical stimulation according to a position and strength of the electromyography signal to selected specific electrical stimulation electrodes 10 in an appropriate time to stimulate the human's limb 70 for designated movements. The control module 50 controls the corresponding electrical stimulation electrodes to generate the electrical stimulation according to the position and status of the received electromyography signal. The electrical stimulation electrodes 10 are pasted to the corresponding muscle.

For example, a patient that has hemiparesis or hemiplegia in the upper limb receives an instruction from a rehab therapist to move a rehabilitation cup from a position to another for training the paralysis or affected limb. The control module 50 detects the upper arm of the patient having no ability to raise volitionally by the electromyography signal and the volitional electromyography signal. When the strength of the volitional electromyography signal is lower than the required strength to raise the upper arm, the control module 50 controls the electrical stimulation output unit 30 to provide the electrical stimulation to proper electrical stimulation electrodes 10. The electromyography signal sensor 20 then detects the electromyography signals instantly and transfers the electromyography signals to the control module 50. The control module 50 may instantly adjust the electrical stimulation output to the upper arm, making the patient move the upper limb smoothly.

Thus, the required electrical stimulation corresponding to designated movements in the rehabilitation courses may be provided or predefined during training, for example, pushing out the upper arm and opening the palm. Practically, the control module 50 may be a microprocessor the upper arm and opening the palm. Practically, the control module 50 may be a microprocessor circuit module or a programmable chip. The control module 50 defines intensities of the electrical stimulation by using the electromyography signal. The control module 50 defines the intensity of the electrical stimulation by a comparison method or a look-up table method. The comparison method or the look-up table method compares the reading electromyography signal and a stored standard of the electromyography signal and, then, outputs an appropriate electrical stimulation according to the result of the comparison. The stored standard of the electromyography signal is an electromyography signal value of a healthy limb of the patient with hemiparesis or hemiplegia or an average electromyography signal value of human.

Furthermore, the comparison method or the look-up table method has at least one adjustable parameter. The adjustable parameter may be defined by the medical professional or the user. The mode for carrying out of the adjustable parameter setting is based on the maximum voluntary contraction of the user, and the system outputs an appropriate intensity of the electrical stimulation or increases the intensity of the electrical stimulation by each output according to the differences between each electromyography signal analyzed result and the maximum voluntary contraction. The other mode for carrying out of the adjustable parameter setting is to separate the electromyography signal into several layers and decide an appropriate intensity of the electrical stimulation or the increase intensity of the electrical stimulation by each output according to which layer the electromyography signal lies in.

The fixed brace 60 is used to connect each one of the electrical stimulation electrodes 10, each one of the electromyography signal sensors 20, the electrical stimulation output unit 30, the electromyography signal operation unit 40 and the control module 50 respectively. The fixed brace 60 is designed to attach to the human's limb 70 and is shaped according to the different positions of the human's limb 70. In the present embodiment, the fixed brace 60 is suitable for the upper limb, which comprises an upper arm fixed portion 62, a forearm fixed portion 64 and a palm fixed portion 66. The upper arm fixed portion 62, the forearm fixed portion 64 and the palm fixed portion 66 are shaped respectively corresponding to the upper arm, the forearm and the palm of human and are separately attached to the upper arm, the forearm and the palm. Each of the electrical stimulation electrodes 10 and each one of the electromyography signal sensors 20 are located inside the fixed brace 60. Therefore, when the patient wears the fixed brace 60, each one of the electrical stimulation electrodes 10 and each one of the electromyography signal sensors 20 can attach to the surface of the skin of the patient.

Furthermore, to judge the condition of paralysis of the patient's upper arm's movement more precisely, the control module 50 may analyze each one of the electromyography signal sensors according to the above-mentioned description or detect the curvature of partial or each one of the limb joints with the flex/band sensors on the fixed brace 60 according to the corresponding position of the joints of the wrists, fingers, elbows and arms. Through detecting results of each one of the flex/band sensors, the control module 50 is able to define the condition of the upper arm of the patient and to control each one of the electrical stimulation electrodes 10 through the electrical stimulation output unit 30 to output the electrical stimulation to the patient for suitable assistance.

The shape of the flex/band sensor is usually rod-shaped or bar-shaped. The flex/band sensor generates a different resistance according to the curvature thereof. For example, the flex/band sensor of the embodiment is a product by Spectra Symbol Company. Resistance of the flex/band sensor is 10KΩ under a non-curvature. The resistance increases from 30Ω to 40Ω as the curvature increases, which is shown in Table 1.

TABLE 1

| Resistance | Approximately equal to 9KΩ | Approximately equal to 14KΩ | Approximately equal to 22KΩ |
|---|---|---|---|
| Degree of curvature | Straight line | 90 degree | 180 degree |

Thus, the present embodiment may automatically define the required intensity of the electrical stimulation for the human's limb 70 to perform designated movements according to the detected strength of the electromyography signal of the human's limb 70. The present embodiment can give appropriate assistance to the patient, and it not only activates the patient's partially disabled limb effectively, but also is helpful for training the ability of controlling the affected limb of the patient.

The above mentioned is the embodiment of the present invention only, and not a limitation of the present invention in anyway. Although the present invention discloses the embodiment as above, it's not used to limit the present invention. Every technician familiar with this profession can use the technical content to make some changes or modify it to achieve an equivalent embodiment.

What is claimed is:

1. A wearable upper limb electrical stimulation device with feedback control function comprising:
   multiple electrical stimulation electrodes;
   multiple electromyography signal sensors;
   an electrical stimulation output unit;
   an electromyography signal acquisition unit;
   an electromyography signal operation unit; and
   a control module, wherein:
   each one of the multiple electrical stimulation electrodes is adapted to be pasted or attached to a human's limb, and an electrical stimulation is adapted to be given to a neuromuscular system of the human's limb by each one of the multiple electrical stimulation electrodes;
   each one of the multiple electromyography signal sensors is adapted to be pasted or attached to the human's limb and adapted to be set on a corresponding position of the neuromuscular system of the human's limb;

each electromyography signal sensor senses and receives a electromyography signal that is adapted to be generated by the human limb, wherein each electromyography signal comprises a volitional electromyography signal, a stimulus electromyography signal and an interference signal;

the electrical stimulation output unit is connected with each one of the multiple electrical stimulation electrodes and provides the electrical stimulation;

the electromyography signal acquisition unit is connected with the multiple electromyography signal sensors and receives the electromyography signal;

the electromyography signal acquisition unit filters and enhances the electromyography signal;

the electromyography signal operation unit is connected with the electromyography signal acquisition unit and receives the electromyography signal which has been filtered and enhanced;

the control module is connected with the electrical stimulation output unit and the electromyography signal operation unit;

the control module receives the electromyography signal filtered and enhanced by the electromyography signal operation unit and controls the electrical stimulation output unit to provide electricity to more than one electrical stimulation electrode of the multiple electrical simulation electrodes, according to a position and a strength of the electromyography signal sensed and received by each electromyography signal sensor;

the electromyography signal acquisition unit thereof comprises:
   an electrical stimulation signal blocking circuit;
   an instrumentation amplifier;
   an amplifier circuit;
   a high-pass and low-pass filter; and
   a voltage level shifter or a clamp circuit;

the electrical stimulation signal blocking circuit preliminarily filters the electromyography signal sensed and received by each electromyography signal sensor from interference of the electrical stimulation;

the electromyography signal preliminarily filtered by the electrical stimulation blocking circuit is processed by a front-end amplification through the instrumentation amplifier;

the electromyography signal processed by the front-end amplification is enhanced by an amplification ratio through the amplifier circuit;

the low-pass and high-pass filter filters the electromyography signal enhanced by the amplification ratio that is outside a setting range;

the voltage level shifter or the clamp circuit boosts a voltage level of the electromyography signal filtered by the low-pass and high-pass filter; and the wearable upper limb electrical stimulation device with feedback control function further comprises an analog-to-digital converter connected between the voltage level shifter or the clamper circuit and the electromyography signal operation unit;

the analog-to-digital converter digitizes the electromyography signal output from the voltage level shifter or the clamper circuit;

the electromyography signal operation unit receives the electromyography signal that has been digitized by the analog-to-digital converter;

the electromyography signal operation unit comprises:
   an interference operation unit;
   a comb filter; and
   a subtraction circuit;
   after the interference operation unit filters a pulse of the electrical stimulation in the electromyography signal, the comb filter filters the volitional electromyography signal from the electromyography signal; and
   the subtraction circuit uses the electromyography signal sensed and received by each electromyography signal sensor minus the volitional electromyography signal output from the comb filter and produces the stimulus electromyography signal.

2. The wearable upper limb electrical stimulation device with feedback control function as claimed in claim 1, wherein a front-end signal of each electromyography signal is filtered by the interference operation unit.

3. The wearable upper limb electrical stimulation device with feedback control function as claimed in claim 2, wherein a time range of the front-end signal of each electromyography signal sensed and received by each electromyography signal sensor is between 100 μs and 5 ms.

4. The wearable upper limb electrical stimulation device with feedback control function as claimed in claim 3, further comprising a fixed brace whose shape is adapted to correspond to the human's limb, wherein the fixed brace is connected with each one of the multiple electrical stimulation electrodes, each one of the multiple electromyography signal sensors, the electrical stimulation output unit, the electromyography signal operation unit and the control module, and wherein the multiple electrical stimulation electrodes and the multiple electromyography signal sensors are mounted on an inner surface of the fixed brace.

5. The wearable upper limb electrical stimulation device with feedback control function as claimed in claim 4, wherein the fixed brace thereof comprises an upper arm fixed portion, a forearm fixed portion and a palm fixed portion which is adapted to be shaped respectively corresponding to an upper arm, a forearm and a palm of a user, and is adapted to be detachably separately mounted on the upper arm, the forearm and the palm of the user.

6. The wearable upper limb electrical stimulation device with feedback control function as claimed in claim 5, wherein the control module controls the multiple electrical stimulation electrodes to generate the electrical stimulation according to a status and positions of the received electromyography signals sensed and received by each electromyography signal sensor.

7. The wearable upper limb electrical stimulation device with feedback control function as claimed in claim 6, wherein the control module is a micro-processor module or a programmable chip.

8. The wearable upper limb electrical stimulation device with feedback control function as claimed in claim 6, wherein:
   the control module adjusts the electrical stimulation according to the electromyography signal sensed and received by each electromyography signal sensor;
   the control module decides an intensity of the electrical stimulation according to a comparison method or a look-up table method;
   the comparison method or the look-up table method compares the electromyography signal sensed and received by each electromyography signal sensor and a standard electromyography signal, then outputs an electrical stimulation according to a result of the comparison; and the standard electromyography signal is an electromyography signal value of a healthy limb or an average electromyography signal value of a human.

9. The wearable upper limb electrical stimulation device with feedback control function as claimed in claim 6, further comprising multiple flex/band sensors, wherein:
the multiple flex/band sensors are connected to the fixed brace adapted to correspond to joints of the upper arm, the forearm and the palm;
the multiple flex/band sensors sense curvature and output a sensing result to the control module; and
the control module controls a specific electrical stimulation electrode of the multiple electrical stimulation electrodes with the electromyography signal to generate the electrical stimulation according to the sensing result of the multiple flex/band sensors.

10. The wearable upper limb electrical stimulation device with feedback control function as claimed in claim 2, further comprising a fixed brace whose shape is adapted to correspond to the human's limb, wherein the fixed brace is connected with each one of the multiple electrical stimulation electrodes, each one of the multiple electromyography signal sensors, the electrical stimulation output unit, the electromyography signal operation unit and the control module, and wherein the multiple electrical stimulation electrodes and the multiple electromyography signal sensors are mounted on an inner surface of the fixed brace.

11. The wearable upper limb electrical stimulation device with feedback control function as claimed in claim 10, wherein the fixed brace thereof comprises an upper arm fixed portion, a forearm fixed portion and a palm fixed portion which is adapted to be shaped respectively corresponding to an upper arm, a forearm and a palm of a user, and is adapted to be detachably separately mounted on the upper arm, the forearm and the palm of the user.

12. The wearable upper limb electrical stimulation device with feedback control function as claimed in claim 11, wherein the control module controls the multiple electrical stimulation electrodes to generate the electrical stimulation according to a status and positions of the received electromyography signals sensed and received by each electromyography signal sensor.

13. The wearable upper limb electrical stimulation device with feedback control function as claimed in claim 12, wherein the control module is a micro-processor module or a programmable chip.

14. The wearable upper limb electrical stimulation device with feedback control function as claimed in claim 12, wherein:
the control module adjusts the electrical stimulation according to the electromyography signal sensed and received by each electromyography signal sensor;
the control module decides an intensity of the electrical stimulation according to a comparison method or a look-up table method;
the comparison method or the look-up table method compares the electromyography signal sensed and received by each electromyography signal sensor and a standard electromyography signal, then outputs an electrical stimulation according to a result of the comparison; and
the standard electromyography signal is an electromyography signal value of a healthy limb or an average electromyography signal value of a human.

15. The wearable upper limb electrical stimulation device with feedback control function as claimed in claim 12, further comprising multiple flex/band sensors, wherein:
the multiple flex/band sensors are connected to the fixed brace adapted to correspond to joints of the upper arm, the forearm and the palm;
the multiple flex/band sensors sense curvature and output a sensing result to the control module; and
the control module controls a specific electrical stimulation electrode of the multiple electrical stimulation electrodes with the electromyography signal to generate the electrical stimulation according to the sensing result of the multiple flex/band sensors.

16. The wearable upper limb electrical stimulation device with feedback control function as claimed in claim 1, further comprising a fixed brace whose shape is adapted to correspond to the human's limb, wherein the fixed brace is connected with each one of the multiple electrical stimulation electrodes, each one of the multiple electromyography signal sensors, the electrical stimulation output unit, the electromyography signal operation unit and the control module, and wherein the multiple electrical stimulation electrodes and the multiple electromyography signal sensors are mounted on an inner surface of the fixed brace.

17. The wearable upper limb electrical stimulation device with feedback control function as claimed in claim 16, wherein the fixed brace thereof comprises an upper arm fixed portion, a forearm fixed portion and a palm fixed portion which is adapted to be shaped respectively corresponding to an upper arm, a forearm and a palm of a user, and is adapted to be detachably separately mounted on the upper arm, the forearm and the palm of the user.

18. The wearable upper limb electrical stimulation device with feedback control function as claimed in claim 17, wherein the control module controls the multiple electrical stimulation electrodes to generate the electrical stimulation according to a status and positions of the received electromyography signals sensed and received by each electromyography signal sensor.

* * * * *